United States Patent
Nakaya et al.

(10) Patent No.: US 9,922,418 B2
(45) Date of Patent: Mar. 20, 2018

(54) IMAGE PROCESSING DEVICE

(71) Applicant: SHIMADZU CORPORATION, Kyoto-shi, Kyoto (JP)

(72) Inventors: Tomohiro Nakaya, Kyoto (JP); Kazuyoshi Nishino, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 14/911,483

(22) PCT Filed: Aug. 21, 2013

(86) PCT No.: PCT/JP2013/072332
§ 371 (c)(1),
(2) Date: Feb. 11, 2016

(87) PCT Pub. No.: WO2015/025387
PCT Pub. Date: Feb. 26, 2015

(65) Prior Publication Data
US 2016/0203598 A1 Jul. 14, 2016

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/482* (2013.01); *A61B 6/505* (2013.01); *A61B 6/5205* (2013.01);
(Continued)

(58) Field of Classification Search
CPC ......... G06T 7/0012; G06T 2207/30004; G06T 7/0081; G06T 7/0083; G06T 2207/10121;
(Continued)

(56) References Cited

U.S. PATENT DOCUMENTS 6,724,924 B1 * 4/2004 Wei .................. A61B 5/103
382/132
6,850,635 B2 * 2/2005 Gerard ............... G06F 19/321
128/922
(Continued)

FOREIGN PATENT DOCUMENTS

| JP | 10-509075 | 9/1998 |
| JP | 2004-509722 | 4/2004 |

(Continued)

OTHER PUBLICATIONS

Wikipedia article "Cervical vertebrae", Aug. 10, 2012.*
(Continued)

*Primary Examiner* — Jonathan S Lee
(74) *Attorney, Agent, or Firm* — Andrew F. Young, Esq.; Lackenbach Siegel, LLP

(57) ABSTRACT

An image processing method provides a step of detecting the pedicle region of vertebral arch detects the region having the higher pixel value compared to the periphery thereof is detected by classifying three classes ABC (detection of the pedicle of vertebral arch) of the step S2. Then, in the case of a failure to detect the intervertebral region, e.g., when the intervertebral region is crushed, the boundary, contacting to the cervical vertebra side of the pedicle of vertebral arch detected by the step of classifying three classes ABC (detecting the pedicle of vertebral arch) described above is drawn by classifying ABC three classes (drawing the boundary) of the step S2. Accordingly, even when the intervertebral region is crushed or when the intervertebral region is undetectable, the boundary between the vertebral bodies can be detected accurately. Therefore, the detection performance of the correct boundary is enhanced so that it can also be effective on that the manual correction frequency by the user decreases and the throughput increases.

5 Claims, 13 Drawing Sheets

(51) Int. Cl.
    *A61B 6/00*     (2006.01)
    *G06T 7/12*     (2017.01)

(52) U.S. Cl.
    CPC .............. *G06T 7/0081* (2013.01); *G06T 7/12*
        (2017.01); *G06T 2207/10121* (2013.01); *G06T*
        *2207/30012* (2013.01)

(58) Field of Classification Search
    CPC ...... G06T 2207/30012; G06K 2209/05; A61B
                                        6/482; A61B 6/505
    See application file for complete search history.

(56) References Cited

U.S. PATENT DOCUMENTS

| | | | |
|---|---|---|---|
| 6,904,163 B1 | 6/2005 | Fujimura et al. | |
| 7,010,151 B2 | 3/2006 | Wei et al. | |
| 7,561,728 B2 * | 7/2009 | Abufadel | G06T 7/12 382/132 |
| 8,908,832 B2 | 12/2014 | Yamashita | |
| 8,965,083 B2 * | 2/2015 | Ben Ayed | G06T 7/0081 382/128 |
| 8,983,029 B2 | 3/2015 | Hasegawa | |
| 9,064,307 B2 * | 6/2015 | Ayed | G06T 7/0014 |
| 9,125,619 B2 | 9/2015 | Yabugami | |
| 2002/0061126 A1 * | 5/2002 | Gerard | G06F 19/321 382/128 |
| 2010/0086185 A1 * | 4/2010 | Weiss | B60R 25/00 382/131 |
| 2011/0130653 A1 * | 6/2011 | Wang | A61B 6/505 600/425 |
| 2012/0078255 A1 * | 3/2012 | Bleich | A61B 17/1671 606/79 |
| 2012/0143090 A1 * | 6/2012 | Hay | A61B 6/505 600/587 |
| 2013/0076157 A1 * | 3/2013 | Stein | A61F 2/442 307/116 |
| 2013/0077840 A1 * | 3/2013 | Blumfield | G06F 19/321 382/131 |

FOREIGN PATENT DOCUMENTS

| | | |
|---|---|---|
| JP | 2009-524488 | 7/2009 |
| JP | 2011-131040 | 7/2011 |
| JP | 2013-52121 | 3/2013 |
| WO | WO 02/27635 | 4/2002 |

OTHER PUBLICATIONS

Štern, Darko, et al. "Parametric modelling and segmentation of vertebral bodies in 3D CT and MR spine images." Physics in medicine and biology 56.23 (2011): 7505.*
U.S. Appl. No. 14/759,353, filed Jul. 6, 2015, Okuno.
U.S. Appl. No. 14/785,758, filed Oct. 20, 2015, Sakimoto.
U.S. Appl. No. 14/784,528, filed Oct. 24, 2015, Okuno.
U.S. Appl. No. 13/719,032, filed Dec. 18, 2012, Takahasi.
U.S. Appl. No. 13/995,872, filed Aug. 20, 2013, Kogame.
U.S. Appl. No. 14/157,120, filed Jan. 16, 2014, Okamura.
U.S. Appl. No. 14/363,345, filed Jul. 15, 2014, Ishikawa.
U.S. Appl. No. 14/416,412, filed Jan. 22, 2015, Ishikawa.
U.S. Appl. No. 14/668,354, filed Mar. 25, 2015, Tanaka.
U.S. Appl. No. 14/754,056, filed Jun. 29, 2015, Tanaka.
U.S. Appl. No. 14/760,152, filed Jul. 9, 2015, Tanaka.
U.S. Appl. No. 14/798,991, filed Jul. 14, 2015, Shirota.
U.S. Appl. No. 14/830,187, filed Aug. 19, 2015, Kawabe.
U.S. Appl. No. 14/764,018, filed Jul. 28, 2015, Kakio.
U.S. Appl. No. 14/785,737, filed Oct. 20, 2015, Watanabe.
U.S. Appl. No. 14/766,522, filed Aug. 7, 2015, Okuno.
PCT/JP2013/072332, International Search Report and Written Opinion, 2 pages—English, 6 pages—Japanese.
The Gold Standard of X-ray Bone Density Measuring Apparatus, Hologice, Inc., Lawrence Jablonski, et al. (2006), Quantifying Image Quality of DXA Scammers Performing Vertebral Fracture Assessment Living Radiographic Phantoms, 2 pages—English, 6 pages—Japanese.
Prodigy for Bone Health, www3.gehealthcare.com/en/About_US/Subscribe_to_Smartmail, 2013 General Electric Company, 13 pages—English; 15 pages—Japanese.
Raising the bar in skeletal health imaging, www.hologic.com/en/skeletal/osteoporosis-asssessment/discovery.

* cited by examiner

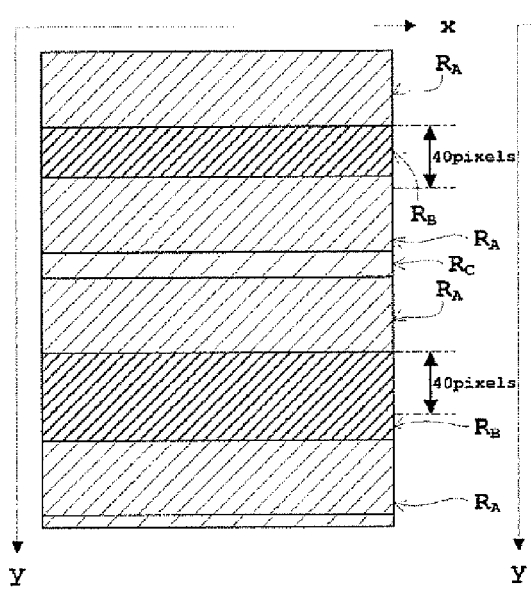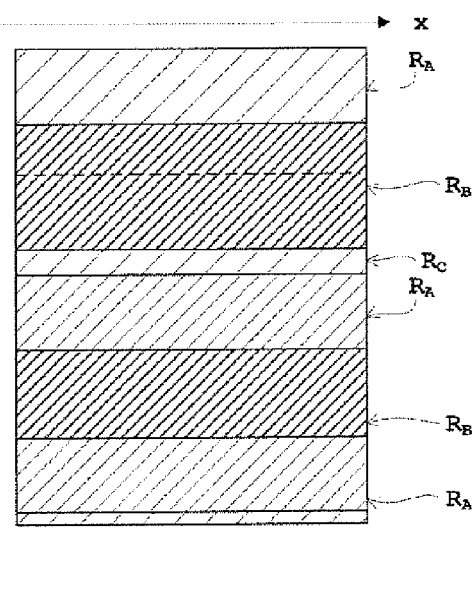

IMAGE PROCESSING DEVICE

CROSS REFERENCE TO RELATED APPLICATIONS

This application relates to, claims priority from, and is a national phase filing of Ser. No. PCT/JP2013/072332 filed Aug. 21, 2013, the entire contents of which are incorporated herein by reference

TECHNICAL FIELD

The present invention relates to an image processing method operative to conduct an image processing and particularly relates to a technology that automatically extracts the region of vertebral body.

BACKGROUND

According to the method that automatically extracts the region of vertebral body, a medical image incorporating the spinal column obtained by using an X-ray fluoroscopic apparatus and a bone density measuring apparatus and so forth is employed. Hereafter, the inventors set forth the present invention based on a bone-density measuring apparatus as an example.

Relative to the bone-density measuring apparatus, e.g., DXA (Dual Energy X-Ray Absorptiometry) method employs an X-ray beam having two different energy peaks to conduct the measurement. Specifically, an image selectively imaging only bone (low-dose X-ray image) by imaging the lumbar vertebra of a subject (patient) while lying down and bending the knee on the table. The area of an individual vertebra body must be obtained accurately to measure bone density, such as e.g., the bone mineral content, which is an index, indicating the content of minerals contained in bone, which are (e.g., potassium and phosphorus) contained in a specific amount of bone. Then, technologies to automatically extract the area of vertebral body are proposed (e.g., refer to Patent Documents 1-3 and Non-Patent Documents 1-3.)

The extraction of the region roughly comprises two steps including (1) the step of detecting the profile (sideline) and (2) the step of extracting an individual vertebral body by detecting the boundary between vertebral bodies adjacent each other. The present invention relates to the step (2) set forth above. In addition, referring to FIG. 13, the spinal column extends up-and-down in between the cervical vertebra and the pelvis and there is an intervertebral region (intervertebral disc) C in between the vertebral bodies A adjacent each other in addition to the vertebral body A. The boundary between the vertebral bodies A can be detected by drawing a line at the center of the intervertebral region C. Conventionally relative to (2) set forth above, it is deemed that e.g., the pixel values of the constriction location of the profile (sideline) of the lumbar vertebra and of the intervertebral region (when displayed on the monitor, the gradation process renders the pixel value to "brightness") are low; and the boundary between the vertebrae is being detected by contrast between the vertebrae and by the edge information of upper and lower ends of the vertebrae. In addition, according to the present specification, the pixel value and brightness are taken care equally unless otherwise particularly defined.

In addition, a region called "pedicle of vertebral arch" appears both sides of the upper vertebral body. The pedicle of vertebral arch appears almost always in the upper vertebral body and provides with the higher pixel value than the periphery thereof. According to Patent Document 1, Patent Publication JP 2004-509722 Patent Gazette, the pedicle of vertebral arch is extracted as a landmark, the entire contents of which are incorporated herein by reference.

PRIOR ART

Patent Document

Patent Document 1
Patent Publication JP 2004-509722 Patent Gazette
Patent Document 2
JP 2011-131040 A
Patent Document 3
U.S. Pat. No. 7,010,501 B Specification

Non-Patent Document

Non-Patent Document 1
"Prodigy for Bone Health", [online], GE Healthcare, <URL: http://www3.gehealthcare.com/en/Products/Categories/Bone_Health/DXA/Prodigy_for_Bone_Health#tabs/tab4EA97F28C16A4A7FBDAF86CC8F673F6B>
Non-Patent Document 2
"Discovery: X-ray Bone-Density Measuring Apparatus", [online], Toyo Medic Co., Ltd.<URL: http://www.toyo-medic.co.jp/seihin/catg01/discovery.html>
Non-Patent Document 3
"Raising the bar in skeletal health imaging", [online], HOLOGIC, <URL: http://www.hologic.com/en/skeletal/osteoporosis-assessment/discovery/>

ASPECTS AND SUMMARY OF THE PRESENT INVENTION

Aspects to be Solved

Nevertheless, it is problematic that the boundary between the vertebral bodies may not be drawn or may be erroneously drawn, when the intervertebral region is crushed or when the intervertebral region may not be detected, Considering such circumstances, one aspect of the present invention is to provide an image processing method for extracting accurately the boundary between the vertebral bodies.

Means for Solving the Problem

The present invention comprises the following structure to solve such problem.

Specifically, the image processing method of the present invention is an image processing method to conduct the image processing comprising the steps of; detecting the pedicle of vertebral arch, wherein the region of the pedicle of vertebral arch of vertebral body is detected, and drawing the boundary, wherein the boundary contacting to the cervical vertebra side of the pedicle of vertebral arch detected by the step of detecting the pedicle of vertebral arch is drawn; and that specifies the boundary drawn by the step of drawing the boundary as the boundary between the vertebra bodies adjacent each other.

According to the image processing method of the present invention, the region of the pedicle of vertebral arch, which is almost always observed at the upper portion of vertebral body (the cervical vertebra side of the vertebra body) and provides the higher pixel value compared to the periphery thereof, is detected in the step of detecting the pedicle of vertebral arch. Then, in the case of a failure to detect the intervertebral region, e.g., when the intervertebral region is crushed, the boundary contacting to the cervical vertebra side of the pedicle of vertebral arch detected by the step of detecting the pedicle of vertebral arch, as described above, is drawn by the step of drawing the boundary. Accordingly, even when the intervertebral region is crushed or when the intervertebral region is undetectable, the boundary between the vertebral bodies can be detected accurately. Therefore, the detection performance of the correct boundary is enhanced so that it can also be effective on that the frequency of manual correction by the user decreases and the throughput increases.

The image processing method described above comprises the step of classifying the region; wherein the region of the pedicle of vertebral arch is specified as the region A, the region of vertebral body excluding the region A is specified as the region B and the intervertebral region is specified as the region C; and each vertebral body is classified to the region A described above, the region B described above and the region C described above. Then, if there is the region C described above, the boundary between the vertebral bodies is drawn in the region C. and even if there is no region C, the transition location from the region B to the region A is preferably specified as the boundary between the vertebral bodies when the region B and the region A are classified tandem and sequentially from the cervical vertebra toward the pelvis. The step of classifying the region can accurately classify the region A, the region B and the region C, and even if there is no region C (i.e., when the intervertebral region is crushed or when the intervertebral region is undetectable), the transition location from the region B to the region A is specified as the boundary between the vertebral bodies so that the boundary between the vertebral bodies can be detected further accurately.

When the step of classifying the region described above is included, it is further preferable that the steps are conducted as set forth below.

Specifically, when the step of classifying the regions described above classifies the region A described above, the region B described above and the region C described above, it is preferable that a tripartition is conducted at the attention line in the horizontal direction and the classification is conducted by using the magnitude correlation of each average pixel value between the parts and the magnitude correlation between the moving average pixels relative to the attention line as the center thereof and the average pixel values of the entire attention line. Specifically, the tripartition into the left pedicle of vertebral arch, the center portion without pedicle of vertebral arch and the right pedicle of vertebral arch is conducted by utilizing that the pedicle of vertebral arch appears at both right and left side, and then the region A, the region B and the region C are accurately classified by using the magnitude correlation each other.

In addition, when the step of classifying the regions described above is included, the step can be conducted as set forth below.

Specifically, the step of correcting the regions is included, wherein the step conducts the correction (1) set forth below to the correction (5) set forth below based on the classification results relative to the region A described above, the region B described above and the region C described above.

The correction (1) conducts the correction by which the region A classified to the pelvis side is entirely replaced by the region B when the region A, the region B and the region A are classified tandem and sequentially from the cervical vertebra toward the pelvis and when the length of the region B from the cervical vertebra toward the pelvis is shorter than the predetermined threshold value.

The correction (2) conducts the correction by which the region B is replaced by the region A when the region C, the region B and the region A are classified tandem and sequentially from the cervical vertebra toward the pelvis.

The correction (3) conducts the correction by which the region A is replaced by the region B when the region A, the region B and the region C are classified tandem and sequentially from the cervical vertebra toward the pelvis.

The correction (4) conducts the correction, wherein the longitudinal direction extending between the cervical vertebra and the pelvis is specified as the up-and-down y-direction; the y-coordinate from the region C to the region A or the region B is specified as the upper side of vertebral body when the region A, the region B and the region C are classified tandem and sequentially from the cervical vertebra toward the pelvis as the classification at the time after the correction (3) described above; the y-coordinate from the region A or the region B to the region C is specified as the lower side of vertebral body when the region A, the region B and the region C are classified tandem and sequentially from the cervical vertebra toward the pelvis; the y-coordinate from the region B to the region A is specified as the upper side of the next vertebral body when the region B and the region A are classified tandem and sequentially from the cervical vertebra toward the pelvis; in addition, the (y−1)-coordinate of one previous pixel, which is located in the cervical vertebral side from the upper side of the next vertebral body, is specified as the lower side of vertebral body; the process to divide as the temporal boundary of vertebral body is repeatedly conducted as to the other vertebral bodies; the total length in the y-direction relative to only the vertebral body is obtained from the y-coordinate of the upper side and the lower side of vertebral bodies divided by conducting repeatedly; the value obtained by dividing the total length above by the known number of vertebral bodies of vertebral images is specified as the average length of vertebral body, and each actual length of vertebral body is ranked based on the obtained average length of vertebral body; and the processing to coalesce the vertebral body having the shorter length in order with either upper or lower vertebral body is repeated until no vertebral body less than the predetermined ratio of the average length of vertebral body remains or until the number of the divided vertebral bodies becomes the same as the known number described above.

The correction (5) conducts the correction, wherein the longitudinal direction extending between the cervical vertebra and the pelvis is specified as the up-and-down y-direction; each distance between right and left of the sideline profiling the vertebral body per pixel line along the boundary, which is adjacent to definite number of pixels each other up-and-down from the boundary as the center at the y-coordinate from the region B to the region A, is obtained when the region B and the region A are classified sequentially from the cervical vertebra toward the pelvis; the y-coordinate is obtained at the pixel line having the shortest distance; and the correction relative to the y-coordinate as the boundary from the region B to the region A is newly conducted.

In this way, the step of correcting the regions can only detect the correct boundary, excluding the boundary of vertebral body that should not be naturally detected, by conducting each correction (1)-(5) set forth above. In addition, the correction (4) set forth above each actual length of vertebral body is ranked based on the obtained average length of vertebral body; the processing to coalesce the vertebral body having the shorter length in order with either upper or lower vertebral body is repeated so that the generation of vertebral body abnormally long in the longitudinal direction due to coalescence is prevented. In addition, the accuracy of the boundary detection can be improved due to the correction (5) set forth above. Further, the order of the corrections, (1)-(5) set forth above, is not particularly limited but the correction (4) set forth above should be conducted following the correction (3) set forth above. However, it is preferable that the correction (1) set forth above, the correction (2) set forth above, the correction (3) set forth above, the correction (4) set forth above, the correction (5) set forth above are conducted in order under consideration of the prevention of the generation of an abnormally long vertebral body in the longitudinal direction.

With regard to the image processing of the present invention described above, it is preferable that the step of correcting the boundary is included.

Specifically, it is preferable that in the case of a failure to detect the intervertebral region, when the boundary contacting to the cervical vertebra side of the pedicle of vertebral arch detected by the step of detecting the pedicle of vertebral arch described above is specified as the boundary between adjacent vertebral bodies each other, the step of correcting the boundary obtains each distance between right and left of the sideline profiling the vertebral body per pixel line that is respectively adjacent to definite number of pixels at the cervical vertebra side and the pelvis side from the boundary as the center and along the boundary, the pixel line having the shortest distance is newly corrected as the boundary between adjacent vertebral bodies each other. The accuracy of the boundary detection can be improved as well as the correction (5) set forth above.

Effect of the Invention

According to the image processing method of the present invention, the step of detecting the region of pedicle of vertebral arch detects the region having the higher pixel value compared to the periphery thereof. Then, in the case of a failure to detect the intervertebral region, e.g., when the intervertebral region is crushed, the boundary contacting to the cervical vertebra side of the pedicle of vertebral arch detected by the step of detecting the pedicle of vertebral arch, as described above, is drawn by the step of drawing the boundary. Accordingly, even when the intervertebral region is crushed or when the intervertebral region is undetectable, the boundary between the vertebral bodies can be detected accurately.

BRIEF DESCRIPTION OF THE DRAWINGS

FIGS. 7A, 7B are schematic diagrams relative to results correction (correction of the region correction (1)) of the step S3 of FIG. 2.

PREFERRED EMBODIMENTS OF THE PRESENT INVENTION

Figure 1:
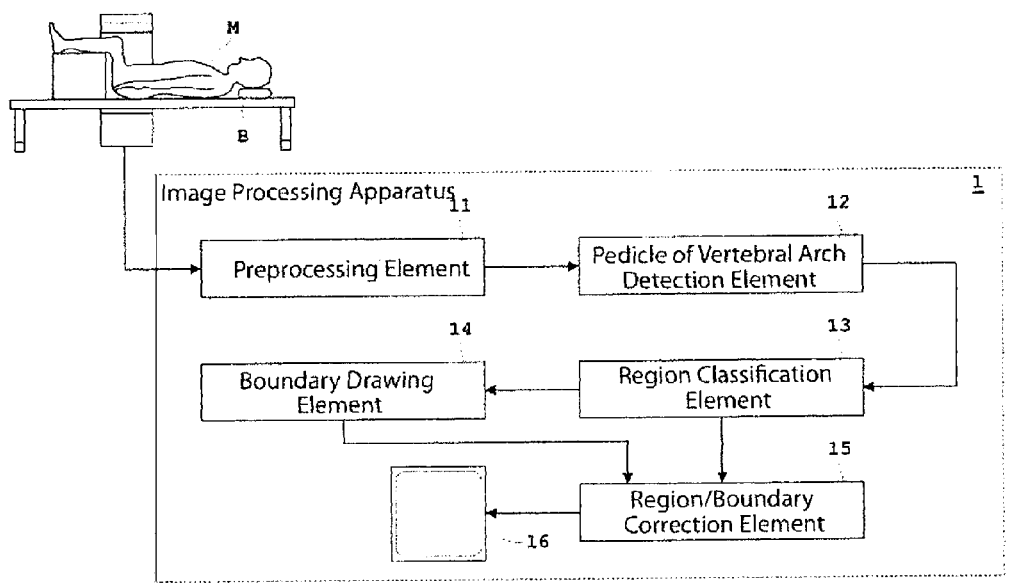
FIG. 1 is a block diagram illustrating the system of the image processing apparatus of Embodiment.

Referring now to the Figures, the inventors illustrate an exemplary Embodiment of the present invention. FIG. 1 is a block diagram illustrating the system of the image processing apparatus of Embodiment. Referring to FIG. 1, the inventors illustrate an Embodiment referring to the case in which an X-ray attenuation image incorporates the spinal column obtained by a bone-density measuring apparatus.

Referring to FIG. 1, the image processing apparatus comprises; a GPU (graphics processing unit), a central processing unit (CPU) or a programmable device (e.g., FPGA (field programmable gate array) of which a hardware circuit (e.g., a logic circuit) used inside is changeable corresponding to the program data, and an input element is structured by a pointing device represented by a mouse, a keyboard, a joystick, a trackball and a touch panel.

Referring to FIG. 1, the image processing apparatus of the present Embodiment comprises; a preprocessing element 11, a pedicle of vertebral arch detection element 12, a region classification element 13, a boundary drawing element 14 and a region/boundary correction element 15; and a display element 16 to output and display each image. Referring to FIG. 1, while the region corrected by the region/boundary correction element 15 and the image having the drawn boundary (between the vertebral bodies) are output and displayed on the display element 16; actually, each image obtained by the preprocessing element 11, the pedicle of vertebral arch detection element 12, the region classification element 13 and the boundary drawing element 14 is output to and displayed on the display element 16. The inventors set forth in detail referring to FIG. 2 and later relative to a specific function of the preprocessing element 11, the pedicle of vertebral arch detection element 12, the region classification element 13, the boundary drawing element 14 and the region/boundary correction element 15.

Figure 2:
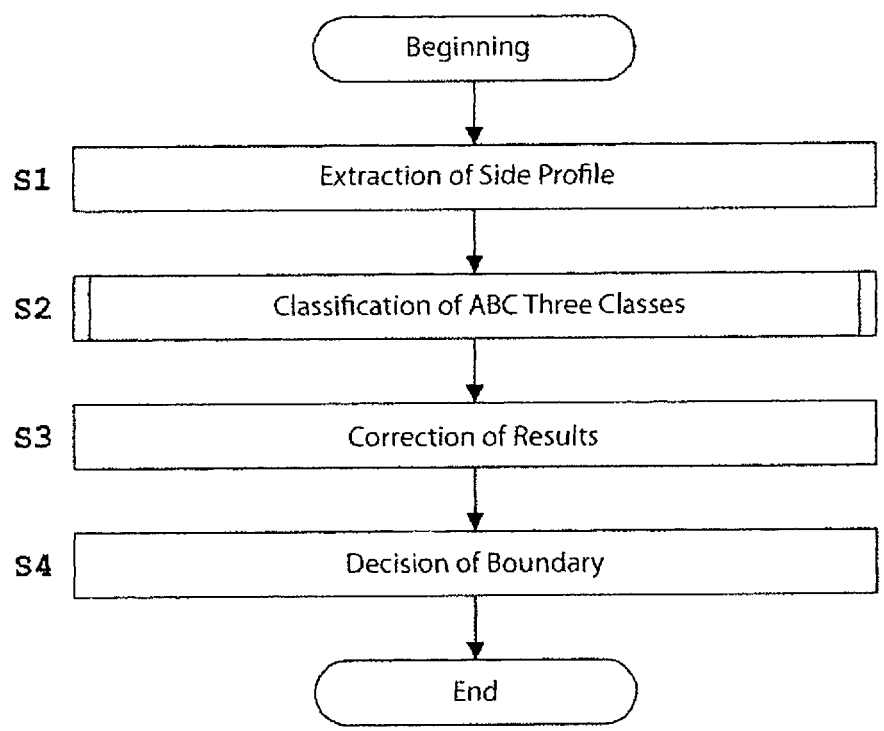
FIG. 2 is a flow chart of a series illustrating the flow of the image processing method of the present invention.
Figure 3:
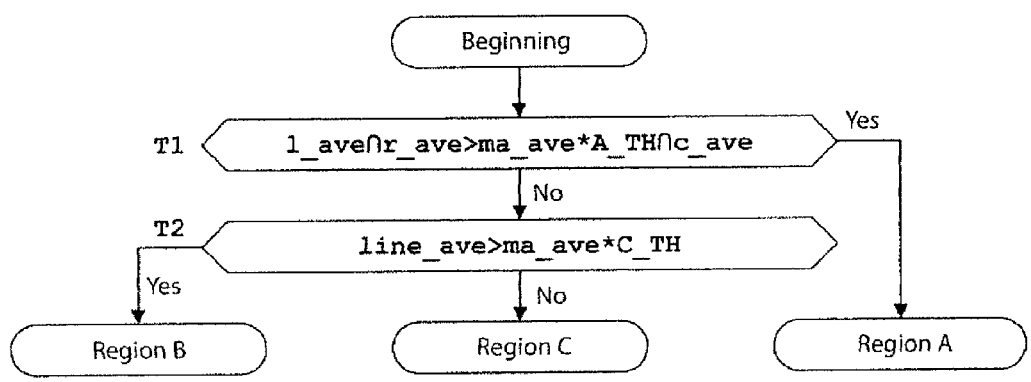
FIG. 3 is a specific flow chart of magnitude correlation relative to the ABC three classes (region classification) of the step S2 of FIG. 2.
Figure 4:
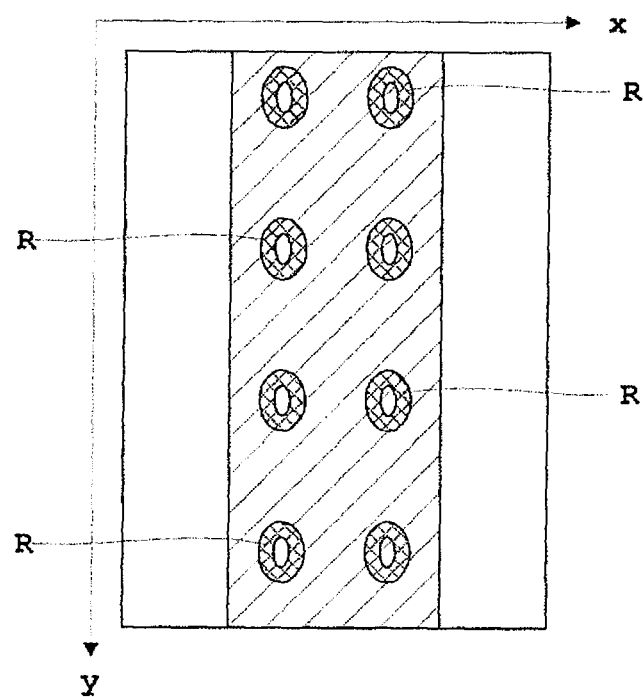
FIG. 4 is a schematic diagram relative to the ABC three classes (detecting of the pedicle of vertebral arch) of the step S2 of FIG. 2.
Figure 5:
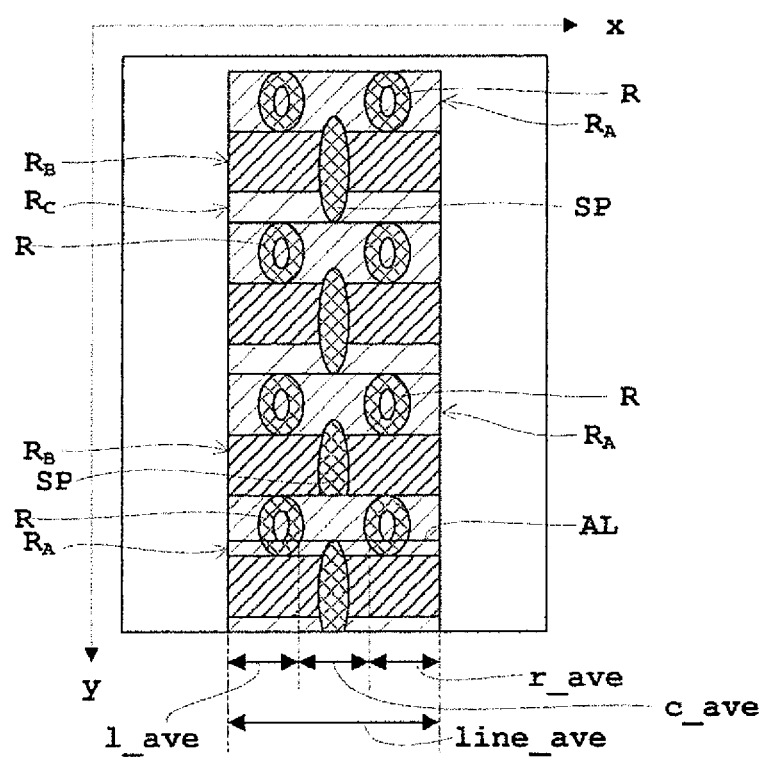
FIG. 5 is a schematic diagram relative to the ABC three classes (region classification) of the step S2 of FIG. 2.
Figure 6:
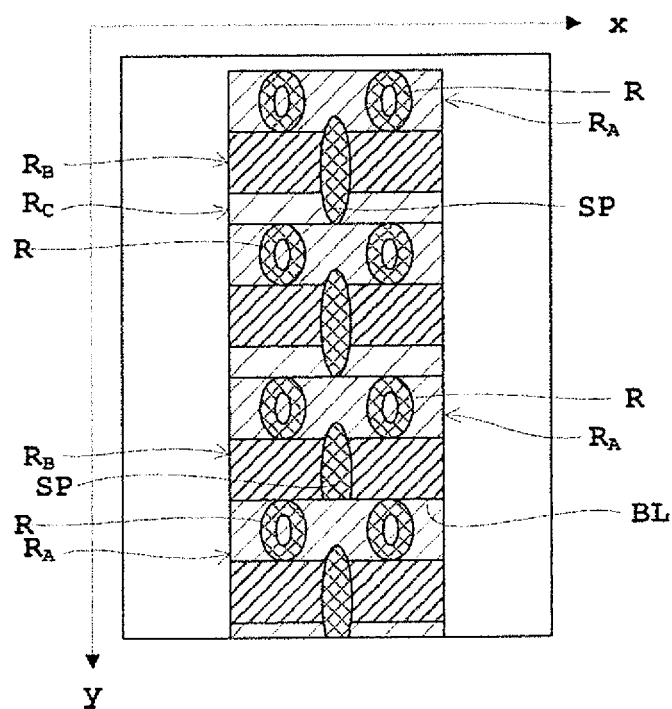
FIG. 6 is a schematic diagram relative to the ABC three classes (drawing the boundary) of the step S2 of FIG. 2 without region C.
Figure 8A:
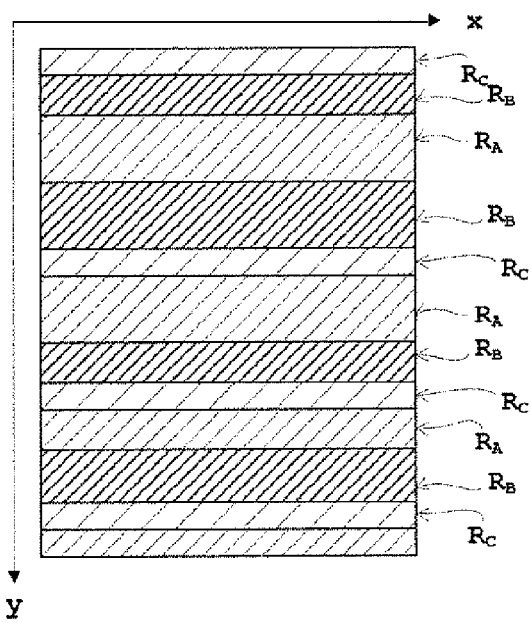
FIGS. 8A, 8B are schematic diagrams relative to results correction (correction of the region correction (2)) of the step S3 of FIG. 2.
Figure 8B:
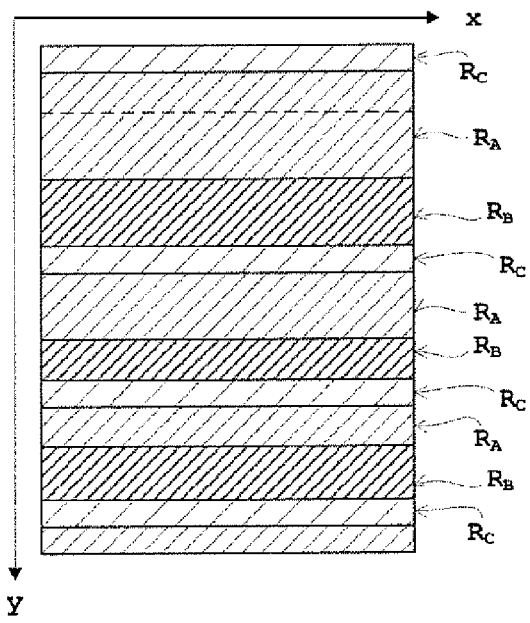
Figure 9A:
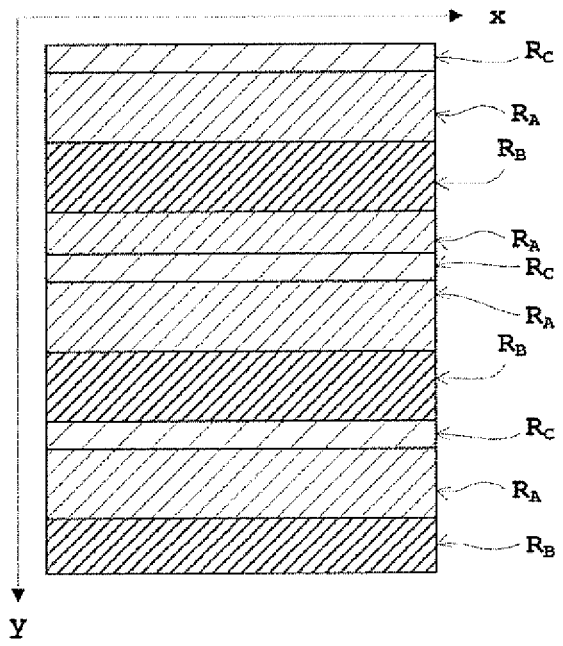
FIGS. 9A, 9B are schematic diagrams relative to results correction (correction of the region correction (3)) of the step S3 of FIG. 2.
Figure 9B:
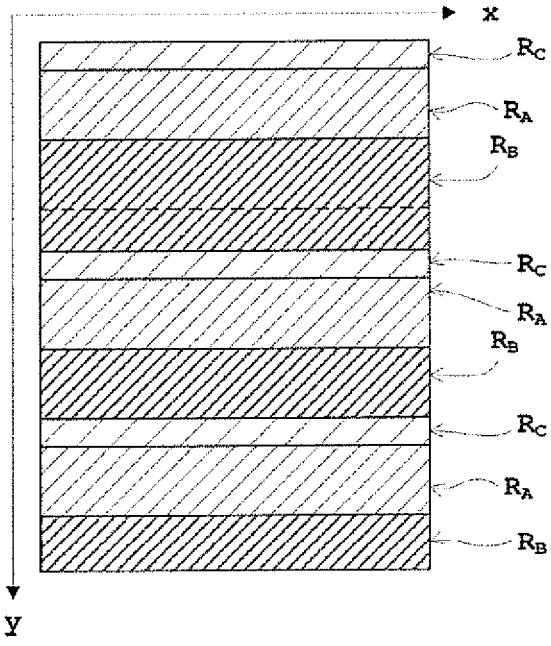
Figures 10A, 10B:
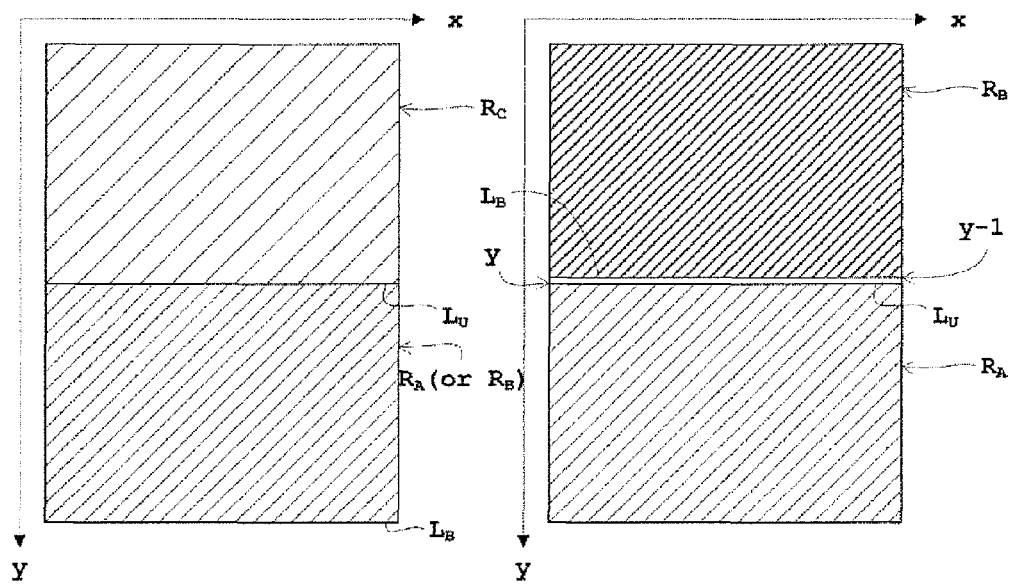
FIGS. 10A, 10B are schematic diagrams relative to results correction (correction of the region correction (4)) of the step S3 of FIG. 2.
Figure 11:
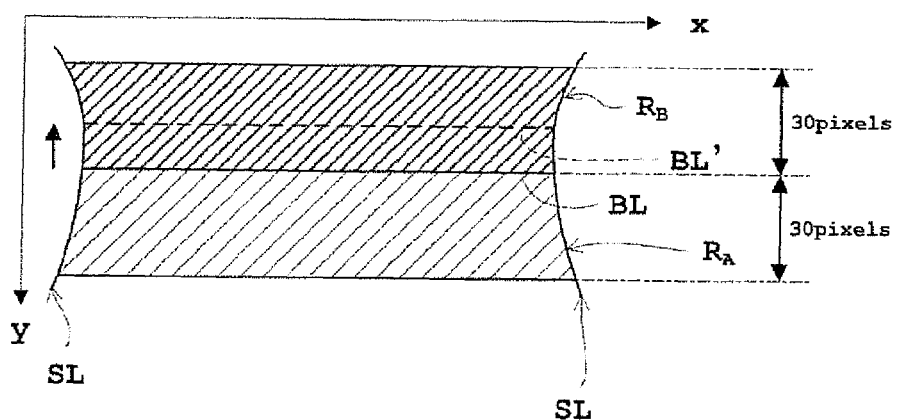
FIG. 11 is a schematic diagram relative to results correction (correction of the region correction (5), the boundary correction) of the step S3 of FIG. 2.
Figure 12:
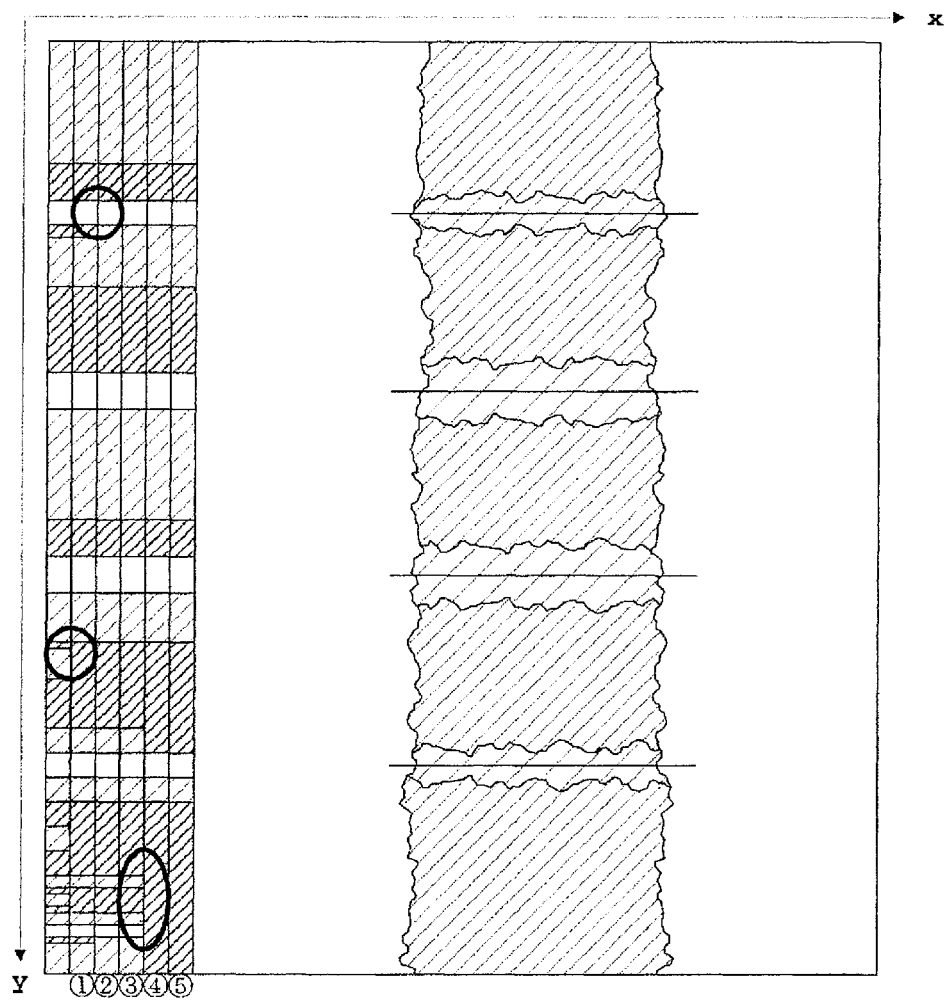
FIG. 12 is a schematic diagram illustrating the classification result correction relative to decision of the boundary of the step S4 of FIG. 2.
Figure 13:
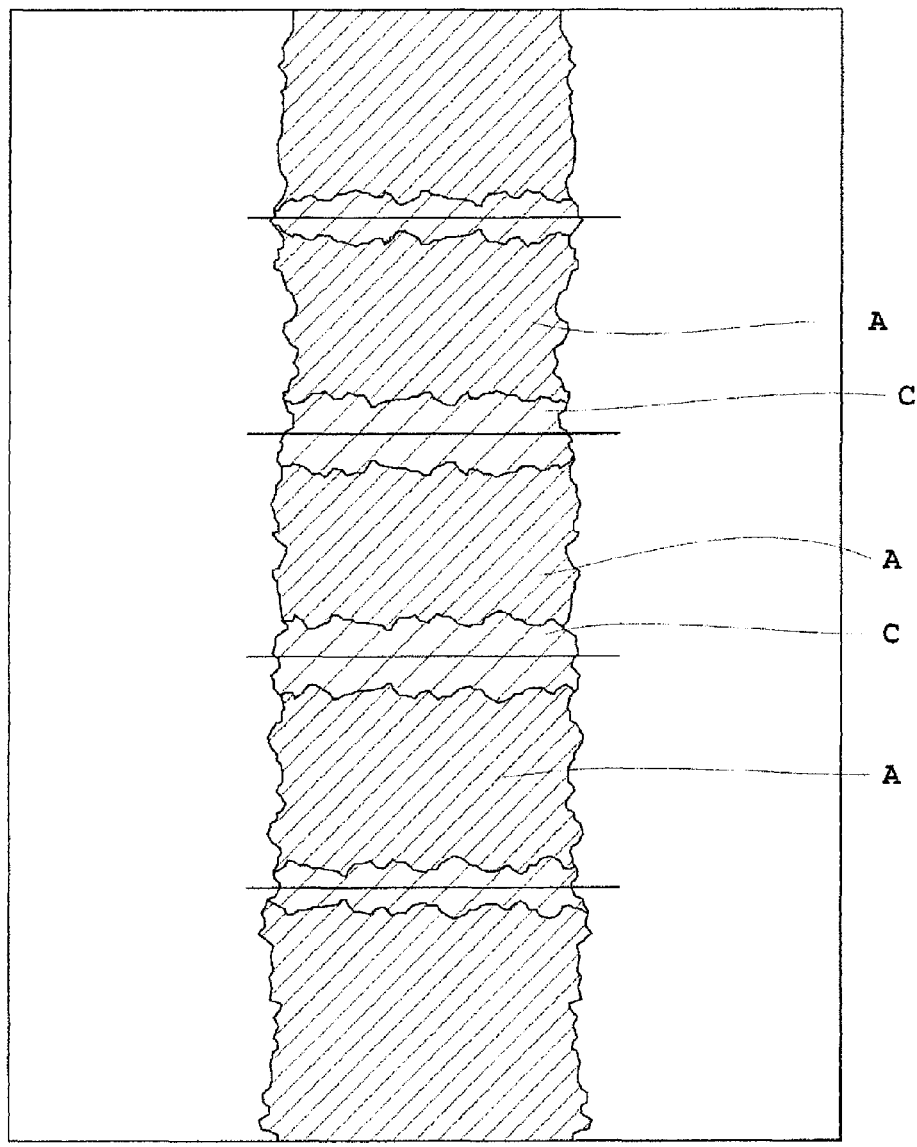
FIG. 13 is a schematic diagram illustrating the vertebral bodies/intervertebral regions relative to the spinal column.

Next, the inventors set forth the specific function of the preprocessing element 11, the pedicle of vertebral arch detection element 12, the region classification element 13, the boundary drawing element 14 and the region/boundary correction element 15 referring to FIG. 2-FIG. 12 along with FIG. 1 described above. FIG. 2 is the flow chart of a series illustrating the flow of the image processing method of Embodiment. FIG. 3 is a specific flow chart of magnitude correlation relative to the ABC three classes (region classification) of the step S2 of FIG. 2. FIG. 4 is a schematic diagram relative to the ABC three classes (detecting of the pedicle of vertebral arch) of the step S2 of FIG. 2. FIG. 5 is a schematic diagram relative to the ABC three classes (region classification) of the step S2 of FIG. 2. FIG. 6 is a schematic diagram relative to the ABC three classes (drawing the boundary) of the step S2 of FIG. 2 without region C. FIGS. 7A, 7B are schematic diagrams relative to results correction (correction of the region correction (1)) of the step S3 of FIG. 2. FIGS. 8A, 8B are schematic diagrams relative to results correction (correction of the region correction (2)) of the step S3 of FIG. 2. FIGS. 9A, 9B are schematic diagrams relative to results correction (correction of the region correction (3) of the step S3 of FIG. 2. FIGS. 10A, 10B are schematic diagrams relative to results correction (correction of the region correction (4) of the step S3 of FIG. 2. FIG. 11 is a schematic diagram relative to results correction (correction of the region correction (5), the boundary correction) of the step S3 of FIG. 2. FIG. 12 is a schematic diagram illustrating the classification result correction relative to decision of the boundary of the step S4 of FIG. 2.

In addition, since the vertebral body region has a high pixel value (brightness) and will appear whity due to the image of vertebral body, and the background region other than the vertebral region has a low pixel value (brightness) and will appear darker, but for convenience sake of illustrating FIGS, the images of FIG. 4-FIG. 12 are schematically illustrated as an inversion image with hatching. Accordingly, the background region having the low pixel value (brightness) is shown as if white and the other region having relatively low pixel value (brightness) is shown as upper right diagonal lines and the region (e.g., the pedicle of vertebral arch and the spinous process) having relatively high pixel value (brightness) is shown as hatching with crossed diagonal lines. In addition, the background of the medical image (original image) is shown as if white, and the vertebral region other than the background is shown as upper right diagonal lines. The pelvis is not shown in FIG. 4-FIG. 12. In addition, referring to FIG. 4-FIG. 12, the horizontal direction is the x-direction (here, the right direction is positive direction) and the extended longitudinal direction between the cervical vertebra and the pelvis is the up-and-down y-direction (the direction toward the pelvis is specified as the positive direction.)

When an imaging is conducted by the bone-density measuring apparatus, first referring to FIG. 1, a subject is laid down on the table B while bending the knee and the X-ray attenuation image is acquired by irradiating the X-ray beam, having two different energy peaks, toward the lumbar vertebra. Further, an X-ray image incorporating the vertebral column acquired by using an X-ray fluoroscopic imaging apparatus can be used. The image processing set forth below is conducted using the X-ray attenuation image acquired by using the bone-density measuring apparatus or the X-ray image acquired by using the X-ray fluoroscopic imaging apparatus.

(Step S1) Extraction of Side Profile

Referring to the flow chart of FIG. 2, the preprocessing element 11 (referring to FIG. 1) conducts the preprocessing of the extraction of side profile relative to the X-ray attenuation image or the X-ray image. The extraction of side profile is a processing to extract the side profile (sideline) constructing the profile of vertebral body and accordingly, if known processing, it is not particularly limited. For example, following the binarization processing, the sideline can be extracted based on the image processed with the line thinning processing using e.g., the shrink processing (also called as an erosion processing) relative to e.g., the morphology operation. Other than that, the sideline can be extracted based on the image processed with enhancement, e.g., the first derivation using the difference of pixels, such as Sobel filter, Robert filter and Laplacian filter, or the secondary derivation using the additional difference of the difference of pixels. The extracted sideline is specified as the sideline SL in FIG. 11 described later.

Relative to the sideline SL, two sidelines right and left are extracted so that the locus of the midpoint relative to the right and left sidelines SL can be extracted as the centerline (not shown in FIG.) The extracted centerline also represents the vertebral body in the longitudinal direction extending between the cervical vertebra and the pelvis.

(Step S3) Classifying ABC Three Classes

The pedicle of vertebral arch detection element 12 (referring to FIG. 1) detects the region of the pedicle of vertebral arch of vertebral body relative to the image preprocessed (side profile extraction) by the step S1. Specifically, the region of the pedicle of vertebral arch, which is almost always observed at the upper portion of vertebral body (the cervical vertebra side of the vertebra body) and provides the higher pixel value compared to the periphery thereof, is detected. The detected region of the pedicle of vertebral arch is the pedicle of vertebral arch R in FIG. 4. Referring to FIG. 4 as well as FIG. 5-FIG. 12, FIGS are schematically shown as a black and white inversion with hatching so that the pixels of the pedicle of vertebral arch R may actually appear whity and the pixels other than that may appear darkly. Accordingly, the actual pixel value of the pedicle of vertebral arch R is high and the pixel value of others is low.

The region of the pedicle of vertebral arch R may be detected based on the image processed with enhancement processing, e.g., a binarization processing and a line thinning processing as well as the extraction of the side profile. Other than that, the region of the pedicle of vertebral arch R may be detected based on the image processed with enhancement, e.g., the first derivation using the difference of pixels, such as Sobel filter, Robert filter and Laplacian filter, or the secondary derivation using the additional difference of the difference of pixels. Needless to say, if the region of the pedicle of vertebral arch R can be detected without enhancement processing, any enhancement processing may not be mandatory. Hereafter, the inventors set forth as the attention line AL (referring to FIG. 5) extends in the right and left direction (horizontal direction.)

Each region of the image is classified to any region of the region A, the region B and the region C following the processing in accordance with the flow chart of FIG. 3 using the attention line AL extending in the right and left direction (horizontal direction.) Specifically, the region classification element 13 (referring to FIG. 1) classifies each vertebral body to the region A, the region B and the region C. Here, the region of the pedicle of vertebral arch R is specified as the region A. the region of vertebral body excluding the region A is specified as the region B and the region between the vertebral bodies is specified as the region C. Referring to FIG. 5, the region A is specified as the region A $R_A$, the region B is specified the region B $R_B$ and the region C is specified as the region C $R_C$.

Specifically, when the step of classifying the region classifies the region A $R_A$, the region B $R_B$ and the region C $R_C$, a tripartition is conducted at the attention line AL in the horizontal direction and the classification is conducted by using the magnitude correlation of each average pixel value between the parts and the magnitude correlation between the moving average pixels relative to the attention line AL as the center thereof and the average pixel values of the entire attention line AL. According to the present Embodiment, the attention line AL is partitioned equally among three and the average pixel value of the attention line AL partitioned equally among three is respectively obtained as the left average pixel value l_ave, the central average pixel value c_ave and the right average pixel value r_ave in order from left. In addition, relative to these classifications, since the spinous process appearing in the center of vertebral body (as the sign SF in FIG. 5) has the higher pixel value compared to the periphery thereof as well as the pedicle of vertebral arch R, a definite number of pixels at the center is not included in the calculation in order to control an impact due to the spinous process. Accordingly. when the central average pixel value is acquired, the definite number of pixels at the center described above is excluded and then the remained pixels are used for the calculation.

Further, the moving average pixel value having the attention line AL as the center is specified as ma_ave. The pixel value obtained by addition average of a few pixels in the vertical direction (longitudinal direction extending between the cervical vertebra and the pelvis), of which the attention line AL is the baseline, is acquired as the moving average pixel value ma_ave. The reason why the moving average pixel value ma_ave is acquired is that the addition average is acquired with uniformity because the region of vertebral bodies has not been decided at this point. Also when the moving average pixel value ma_ave is acquired, the definite number of pixels of the center described above is excluded from the addition average in order to control the impact of the spinous process SP. Other than that, the average pixel value of the entire attention line AL is acquired as line_ave. The pixel value obtained by an addition average of the entire pixels on the attention line AL extending in the horizontal direction is acquired as an average pixel value line_ave of the entire attention line AL (Step T1) l_ave∩r_ave>ma_ave*A_TH∩c_ave Here, the threshold coefficients are respectively specified as A_TH, C_TH. The threshold coefficients A_TH, C_TH are predetermined appropriate values. It is decided whether the condition of the step T1 is satisfied or not every respective attention line AL. If the condition of the step T1 is satisfied ("Yes" in FIG. 3). the target attention line AL to be decided is classified to the region A $R_A$ as belonging to the region A $R_A$. On the other hand, if the condition of the step T1 is not satisfied ("No" in FIG. 3), the step T2 proceeds.

Here, "l_ave∩r_ave>ma_ave*A_TH∩c_ave" indicates that the case satisfies the conditions including that; the left average pixel value l_ave is larger than ma_ave*A_TH; the right average pixel value r_ave is larger than ma_ave*A_TH; the left average pixel value l_ave is larger than the central average pixel value is larger than c_ave; and the right average pixel value r_ave is larger than the central average pixel value c_ave. Accordingly, at least any one of the inequality signs described above is unsatisfied, the next step T2 proceeds. For example, even though the left average pixel value l_ave is larger than ma_ave*A_TH, if the right average pixel value r_ave is not more than ma_ave*A_TH, the left average pixel value l_ave is not more than the central average pixel value is not more than c_ave, or the right average pixel value r_ave is not more than the central average pixel value c_ave, it is decided that as at least one of the inequality sign conditions is unsatisfied, the next step T2 proceeds.

(Step T2) line_ave>ma_ave*C_TH

It is decided whether the condition of the step T1 is satisfied or not relative to the attention line AL that was not classified to the region A $R_A$ by the step T2. Specifically, if the condition of the step T2, under which the average pixel value line_ave is larger than ma_ave*C_TH, is satisfied ("Yes" in FIG. 3), the certain attention line AL is classified to the region B $R_B$ as the target attention line AL to be decided belongs to the region B $R_B$. On the other hand, if the condition of the step T2, under which the average pixel value line_ave is not more than ma_ave*C_TH, is unsatisfied ("No" in FIG. 3), the certain attention line AL is classified to the region C $R_C$ as the target attention line AL to be decided belongs to the region C $R_C$.

Here, the target attention line AL to be decided by the step T1, T2 can be either a plurality of lines or a single line. Here, in accordance with the processing following the flow chart of FIG. 3, each vertebral body is classified to the region A $R_A$, the region B $R_B$ and the region C $R_C$ and then the step S3 of FIG. 2 proceeds. When classifying, referring to FIG. 6, the region C is not specified (i.e., when the vertebral body is crushed or when the region between the vertebral is undetectable), the boundary drawing element 14 (referring to FIG. 1) draws the boundary contacting to the vertebral body side of the pedicle of vertebral arch. Specifically, referring to FIG. 6, when the region B $R_B$ and the region A $R_A$ are classified tandem and sequentially from the cervical vertebra toward the pelvis, the transition location from the region B $R_B$ to the region A $R_A$ is specified as the boundary. Referring to FIG. 6, the drawn boundary is specified as the boundary BL. The step S2 including the steps T1, T2, referring to FIG. 3, corresponds to the step of detecting the pedicle of vertebral arch, the step of classifying the regions and the step of drawing the boundary.

(Step S3) Correction of Results

Returning to the description of the flow chart of FIG. 2, the region/boundary correction element 15 (referring to FIG. 1) conducts the corrections (1)-(5) set forth below based on the classification results relative to the region A $R_A$, the region B $R_B$, and the region C $R_C$.

Referring to FIG. 7A, the correction (1) conducts the correction by which the region A $R_A$ classified to the pelvis side is entirely replaced by the region B $R_B$ when the region A $R_A$, the region B $R_B$ and the region A $R_A$ are classified tandem and sequentially from the cervical vertebra toward the pelvis and when the length of the region B $R_B$ from the cervical vertebra toward the pelvis (the length in the y-direction) is shorter than the predetermined threshold value. The bone density is applied to diagnose an osteoporosis and the subject is an adult female, sensitive to develop an osteoporosis. When the subject is an adult female and the size per pixel is 0.278 mm (0.278 mm/pixel), the threshold value described above is specified as 40 pixels. Accordingly, relative to the present Embodiment, when the length of the region B $R_B$ in the y-direction is less than 40 pixels (shown as "40 pixels" in FIG. 7A, the region A $R_A$ classified to the pelvis side is entirely replaced by the region B $R_B$. Needless to say, the threshold value is not limited to 40 pixels and a threshold value can be adequately preset depending on the size of the target subject and the size per one pixel.

According to the present Embodiment, the correction (1) is followed by the correction (2). The correction (2) conducts the correction by which the region B is entirely replaced by the region A when the region C, the region B and the region A are classified tandem and sequentially from the cervical vertebra toward the pelvis. The correction (2) is skipped when the region C $R_C$, the region B $R_B$, and the region A $R_A$ are not classified tandem and sequentially from the cervical vertebra toward the pelvis.

According to the present Embodiment, the correction (2) set forth above is followed by the correction (3). Referring to FIG. 9A, the correction (3) conducts the correction by which the region A $R_A$ is replaced by the region B $R_B$ referring to FIG. 9B when the region C $R_C$, the region A $R_A$, the region B $R_B$, the region A $R_A$ and the region C $R_C$ are classified tandem and sequentially from the cervical vertebra toward the pelvis., The correction (3) is skipped when the region C $R_C$, the region A $R_A$, the region B $R_B$, the region A $R_A$ and the region C $R_C$ are not classified tandem and sequentially from the cervical vertebra toward the pelvis, The correction (3) set forth above is followed by the correction (4). The correction (4) conducts the correction by which the longitudinal direction extending between the cervical vertebra and the pelvis is specified as the up-and-down y-direction and when the region C $R_C$, the region A $R_A$, or the region B $R_B$ ($R_A$ (or $R_B$)) of FIG. 10A) are classified tandem and sequentially from the cervical vertebra toward the pelvis in accordance with the classification at the time after the correction (3), referring to FIG. 10A, the total length in the y-direction is acquired as set forth below. The y-coordinate from the region C $R_C$ to the region A $R_A$ or the region B $R_B$ is specified as the upper side of vertebral body $L_U$. In addition, the y-coordinate from the region A $R_A$ or the region B $R_B$ to the region C $R_C$ from the cervical vertebra toward the pelvis is specified as the bottom side of vertebral body $L_B$ (the region C $R_C$ is not shown in FIG. 10A.)

Here, FIG. 10B adjacent to FIG. 10A aligns at the pelvis side. Accordingly, when the bottom side of the FIG. 10A is the region A $R_A$, the region B $R_B$ of the same vertebral body to which the region A $R_A$ belongs is the upper region of the FIG. 10B. On the other hand, when the bottom side of the FIG. 10A is the region B $R_B$, the region B $R_B$ coincides with the region B $R_B$ of the upper side of FIG. 10B. Referring to FIG. 10B, when the region B $R_B$ and the region A $R_A$ are classified sequentially from the cervical vertebra toward the pelvis, the y-coordinate from the region B $R_B$ to the region A $R_A$ is specified as the upper side of the next vertebral body $L_U$. In addition, the (y-1)-coordinate of one previous pixel, which is located in the cervical vertebral side from the upper side of the next vertebral body, is specified as the bottom side of vertebral body $L_B$. In this way, the temporal boundaries of vertebral body ($L_U$, $L_B$) are separately provided.

The process to divide as the temporal boundaries of vertebral body ($L_U$, $L_B$) is repeatedly conducted as to the other vertebral bodies. The total length in the y-direction relative to only the vertebral body is obtained from the y-coordinate of the upper side $L_U$ and the bottom side $L_B$ of vertebral bodies divided by conducting repeatedly. Specifically, the total length of vertebral body excluding the region between the vertebral bodies in the y-direction is obtained. The value obtained by dividing the total length described above by the known number of vertebral bodies of vertebral images is specified as the average length of vertebral body. According to the present Embodiment, the images of vertebral body should be classified into five classes so that the known number should be 5. Therefore, according to the present Embodiment, the value obtained by dividing the total length by 5 is specified as the average length of vertebral body. Needless to say, when the vertebral body in the region other than the lumbar vertebra or the region including the lumbar vertebra, the known number is not limited to 5 and the known number can be set in accordance with the images of the target vertebral body. Each actual length of vertebral body is ranked based on the obtained average length of vertebral body in this way.

The processing to coalesce the vertebral body having the shorter length in order with either upper or lower vertebral body is repeated until no vertebral body less than the predetermined ratio of the average length of vertebral body remains or until the number of the divided vertebral bodies becomes the same as the known number described above (here, 5.) In addition, when the shortest vertebral body (closest to the cervical vertebra) is the top vertebral body, such vertebral body is coalesced to the immediate adjacent vertebral body to the pelvis side. In addition, when the shortest vertebral body (closest to the cervical vertebra) is the top vertebral body, such vertebral body is coalesced into the immediate adjacent vertebral body to the pelvis side. When the vertebral body other than that has less than the predetermined ratio of the average length of vertebral bodies, such vertebral body is coalesced in order from the short vertebral body into either upper or lower vertebral body so that the difference from the average length of vertebral bodies can be lessened by coalescing the vertebral body. In addition, according to the present Embodiment, the predetermined ratio described above is 70%. Thus, according to the present Embodiment, when the length of vertebral body other than the top vertebra and the bottom vertebra is less than 70% of the average length of vertebral bodies, such vertebral body is coalesced into either upper or lower vertebral body so as to lessen the difference from the average length of vertebral bodies. Then, such processing is repeated until no vertebral body less than 70% of the average length of vertebral bodies remains or until the number of the divided vertebral bodies becomes 5. Needless to say, the predetermined ratio is not limited to 70% and if just less than 100%, the predetermined ratio can be adequately preset. However, it is preferable that the predetermined ratio is not less than 50% so as to near the average length of vertebral bodies as much as possible.

The correction (4) is followed by the correction (5). Referring to FIG. 11, the correction (5) refers to the pixel line adjacent to definite number of pixels each other up-and-down from the boundary BL, as the center at the y-coordinate from the region B to the region A is obtained when the region B $R_B$ and the region A $R_A$ are classified sequentially from the cervical vertebra toward the pelvis, as the longitudinal direction extending between the cervical vertebra and the pelvis is the up-and-down y-direction. Such pixel lines are in parallel along with such boundary BL. According to the present Embodiment, the definite number of pixel lines is specified as the pixel number of 30 described above. Thus, the present Embodiment refers to the up-and-down 30 pixels ("30 pixels" is shown in FIG. 11) on the y-coordinate (the boundary BL) from the region B $R_B$ to the region A $R_A$ as a line-at-a-time (a unit of the pixel line.) Needless to say, the definite pixel number is not limited to 30 pixels and the definite pixel number can be adequately preset depending on the size of the target subject and the size per one pixel.

Each distance between right and left of the sideline SL profiling the vertebral body per pixel line along the boundary BL described above. The y-coordinate at the pixel line having the shortest distance (i.e., the pixel line having the least number of pixels between right and left at the sideline SL) is acquired. Such y-coordinate is newly corrected as the boundary from the region B $R_B$ to the region A $R_A$. Referring to FIG. 11, the boundary newly corrected is specified as the boundary BL'. Referring to FIG. 11, the boundary BL' is shown as the broken line.

In this way, the corrections (1)-(5) set forth above are conducted. The step S3 corresponds to the step of correcting the region and the step of correcting the boundary.

(Step S4) Decision of the Boundary

The correction of the classification result to decide the boundary in this way is shown in FIG. 12. The right side of FIG. 12 is the medical image (original image) and the left side of FIG. 12 is the result of the correction of classification. The far left of the left side of FIG. 12 is the classification result (the initial classification result) first classified by the ABC classification by the step S2, the second from the far left of the left side of FIG. 12 (shown as the number 1 in the circle of FIG. 12) is following the correction (1), the third from the far left of the left side of FIG. 12 (shown as the number 2 in the circle) of FIG. 12 is following the correction (2), the fourth from the far left of the left side of FIG. 12 (shown as the number 3 in the circle of FIG. 12) is following the correction (3), the fifth from the far left of the left side of FIG. 12 (shown as the number 4 in the circle of FIG. 12) is following the correction (4), and the sixth from the far left of the left side of FIG. 12 (shown as the number 5 in the circle of FIG. 12) is following the correction (5). In addition, the area circled with heavy line indicates that the correction was corrected therein. In addition, it is notable that the correction is being conducted outside the area circled with the heavy line.

In this way, the boundary is drawn relative to the medical image (original image), which is the X-ray attenuation image acquired by using the bone-density measuring apparatus or the X-ray image acquired by using the X-ray fluoroscopic imaging apparatus. In addition, FIG. 12 is showing when the intervertebral region is detectable, but even if e.g., the intervertebral region is crushed, the boundary can be also drawn by conducting the step S1-S4 described above. In addition, since the inventors set forth the attention line AL extending in the right-and-left direction (horizontal direction), the boundary of FIG. 12 is drawn in the right-and-left direction (horizontal direction), but in fact, it is notable that the boundary may tilt more or less up-and-down depending on the extending direction of the attention line. Accordingly, the boundary drawn on classification in fact tilts more or less up-and-down.

According to the image processing method of the present Embodiment, the region of the pedicle of vertebral arch R, which is almost always observed at the upper portion of vertebral body (the cervical vertebra side of the vertebra body) and provides the higher pixel value compared to the periphery thereof, is detected in the ABC three classification in the step S2 (detecting the pedicle of vertebral arch.) Then, in the case of a failure to detect the intervertebral region, e.g., when the intervertebral region is crushed, the boundary, contacting to the cervical vertebra side of the pedicle of vertebral arch detected by the step S2 of classifying three classes ABC (detecting the pedicle of vertebral arch), is drawn by the step S2 of classifying three classes ABC (drawing the boundary.) Accordingly, even when the intervertebral region is crushed or when the intervertebral region is undetectable, the boundary between the vertebral bodies can be detected accurately. Therefore. the detection performance of the correct boundary is enhanced so that it can also be effective on that the frequency of the manual correction by the user decreases and the throughput is improved.

The present Embodiment comprises the step of classifying the ABC three regions; wherein the region of the pedicle of vertebral arch is specified as the region A $R_A$, the region B $R_B$ of vertebral body excluding the region A $R_A$ is specified as the region B $R_B$ and the intervertebral region is specified as the region C $R_C$; and each vertebral body is classified to the region A $R_A$ specified above, the region B $R_B$ specified above and the region C $R_C$ specified above. Then, if there is the region C $R_C$ specified above, the boundary between the vertebral bodies is drawn in the region C $R_C$, and even if there is no region C, the transition location from the region B $R_B$ to the region A $R_A$ is specified as the boundary BL between the vertebral bodies when the region B $R_B$ and the region A $R_A$ are classified tandem and sequentially from the cervical vertebra toward the pelvis. The step of classifying the region can accurately classify the region A $R_A$, the region B $R_B$ and the region C $R_C$, by the ABC three classification due to the step S2 and even if there is no region C (specifically, when the intervertebral region is crushed or when the intervertebral region is undetectable), the transition location from the region B $R_B$ to the region A $R_A$ is specified as the boundary BL between the vertebral bodies so that the boundary between the vertebral bodies can be detected further accurately.

The present Embodiment is conducted as set forth below when the ABC three classifications due to the step S2 is included.

Specifically, according to the ABC three classification due to the step S2 described above; when the step classifies the region A $R_A$ described above, the region B $R_B$ described above and the region C $R_C$ described above, a tripartition (according to the present Embodiment, partition equally to three) is conducted at the attention line AL in the horizontal direction and the classification is conducted by using the magnitude correlation of each average pixel value between the divisions and the magnitude correlation between the moving average pixels relative to the attention line AL as the center thereof and the average pixel values of the entire attention line AL. Specifically, the tripartition is conducted relative to the left pedicle of vertebral arch, the center portion without pedicle of vertebral arch and the right pedicle of vertebral arch by utilizing that the pedicle of vertebral arch R appears at both right and left side. and then the region A $R_A$, the region B $R_B$ and the region C $R_C$ are accurately classified by using magnitude correlation each other.

In this way, the step of correcting the results (correction of regions) can detect only the correct boundary BL, excluding the boundary of vertebral body that should not be naturally detected, by conducting each correction (1)-(5) set forth above. In addition, the correction (4) set forth above ranks each actual length of vertebral body based on the obtained average length of vertebral body; the processing to coalesce the vertebral body having the shorter length in order with either upper or lower vertebral body is repeated so that the generation of vertebral body abnormally long in the longitudinal direction due to coalescence can be prevented. In addition, the accuracy of the boundary BL detection can be improved due to the correction (5) set forth above.

The present invention is not limited to the aspects of adaptive Embodiment set forth above and further, another alternative Embodiment can be adaptively implemented set forth below.

(1) According to the Embodiment described above, the image of vertebral body is the image of the lumbar vertebra, but Embodiment can be applied to the vertebral body of a region other than the lumbar vertebra and the region also including the lumbar vertebra.

(2) According to the Embodiment described above, the steps S1-S4 of FIG. 2 were conducted, but when the intervertebral region is undetectable, the other step is not mandatory if the boundary contacting to the cervical vertebral side of the detected pedicle of vertebral arch R is drawn and the image processing so as to specify such boundary BL as the boundary between vertebral bodies adjacent each other is conducted. For example, when the region A $R_A$, the region B $R_B$ and the region C $R_C$ are classified by the pixel value (brightness) in sonic extent, the step S2 of classifying the regions is not mandatory. In addition, a preprocessing such as the step S1 of extracting the side profile is also not mandatory.

(3) According to the Embodiment described above, the correction of results (correction of region) due to the step S3 was conducted, but when each region is divided corresponding to the number of vertebral bodies and classified preciously, the step S3 of correcting the results (correction of the regions) is not mandatory.

(4) According to the Embodiment described above, the correction of results (correction of region) due to the step S3 was conducted the correction (1)-(5), but when each region is divided corresponding to the number of vertebral bodies, the correction (5) set forth above can be only mandatory. Specifically, in the case of a failure to detect the intervertebral region, when the boundary contacting to the cervical vertebra side of the pedicle of vertebral arch R is specified as the boundary BL between adjacent vertebral bodies each other, each distance between right and left of the sideline adjacent to a definite number of pixels (30 pixels in the case of Embodiment) in each cervical vertebra side and pelvis side of the boundary BL as the center thereof and also profiling the vertebral body per pixel line along the boundary BL is obtained. And the pixel line having the shortest distance can be newly corrected as the boundary BL' between adjacent vertebral bodies each other. Also in this case, the accuracy of detection of the boundary BL can be improved as well as the correction (5) set forth above.

(5) According to the Embodiment described above, the correction (1) set forth above. the correction (2) set forth above, the correction (3) set forth above, the correction (4) set forth above, and the correction (5) set forth above are conducted in order, the order of the corrections (1)-(5) is not particularly limited but the correction (4) set forth above should be conducted following the correction (3) set forth above. However, according to Embodiment described above, it is preferable that the correction (1) set forth above, the correction (2) set forth above, the correction (3) set forth above, the correction (4) set forth above, and the correction (5) set forth above are conducted in order under consideration of the prevention of that an abnormally long vertebral body in the longitudinal direction is generated.

(6) According to the Embodiment described above, when classifying the region A, the region B and the region C, the tripartition equally of the attention line AL is conducted and the classification is conducted by using the magnitude correlation of each average pixel value between three partitioned equally and the magnitude correlation between the moving average pixels relative to the attention line AL as the center thereof and the average pixel values of the entire attention line AL, but it is not absolutely limited to the tripartition equally. For example, such tripartition may be conducted at the location contacting to the pedicle of the left vertebral arch and the location contacting to the pedicle of the right vertebral arch, and then the classification may be conducted by using the magnitude correlation of the average pixel value of each part and the magnitude correlation between the moving average pixels relative to the attention line AL as the center thereof and the average pixel values of the entire attention line AL.

(7) According to the Embodiment described above, the remained pixels, following calculating without the definite number of pixels of the center and excluding the definite number of pixels of the center, is applied for the calculation so as to suppress the impact of the spinous process SP, but if the pixel value of the spinous process SP is not so high or the spinous process does not appear, the definite number of pixels of the center can be included for the calculation.

FIELD OF THE INVENTION

Accordingly, the present invention is suitable when the bone density of vertebral body (e.g., lumbar vertebra) is measured by DXA method.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

R Pedicle of vertebral arch
BL, BL' Boundary
$R_A$ Region A
$R_B$ Region B
$R_C$ Region C
AL Attention line

What is claimed is:

1. An image processing method to conduct an image processing, comprising the steps of:
    detecting a pair of pedicles of a vertebral arch of a vertebral body, wherein a region of the pedicle of said vertebral arch of said vertebral body is detected;
    drawing a boundary, wherein said boundary is contacting to a head side of a pair of the pedicles of said vertebral arch detected by said step of detecting the pedicle of said vertebral arch; and
    specifying a further said boundary drawn by said step of drawing the boundary as a boundary between each respective said vertebra body of a plurality of vertebral bodies adjacent each other.

2. The image processing method, according to claim 1, further comprising the steps of:
    specifying as a region A the pedicle of each said vertebral arch;
    specifying as a region B the region of each said vertebral body excluding the region A;
    specifying as a region C an intervertebral region; and
    classifying each vertebral body respectively to said region A, said region B and said region C, wherein;
        if there is said region C, then the boundary between the respective vertebral bodies is drawn in the region C, and where there is no region C, a transition location from a respective said region B to the region A is specified as the boundary between the respective said vertebral bodies when the region B and the region A are in tandem and sequentially from the cervical vertebra toward a pelvis.

3. The image processing method according to claim 2, wherein:
when said step of classifying respective said regions classifies said region A, said region B and said region C, further comprising the steps of:
conducting a tripartition in a horizontal direction at an attention line; and
conducting said step of classification by using a magnitude correlation of an average of each said average pixel value of each part and a magnitude correlation between an average of each said moving pixels relative to the attention line as the center thereof and an average pixel value of the entire attention line.

4. The image processing method according to claim 2, further comprising: the step of:
correcting the regions A, B, and C, wherein:
the step of correction the regions A, B, and C further comprises the steps of conducting respectively a correction of each region A, B, C by respective steps 1-Z to 5-Z based upon the results of said classification relative to said region A, said region B and said region C classified by said step of classifying the regions; wherein;
a correction step (1-Z) of conducting the correction by which the region A classified to a pelvis side is entirely replaced by the region B, in a case of a shorter length of the region B from the cervical vertebra toward the pelvis than a predetermined threshold value, when the region A, the region B and the region A are classified tandem and sequentially from the cervical vertebra toward the pelvis;
a correction step (2-Z) of conducting the correction by which the region B is entirely replaced by the region A when the region C, the region B and the region A are classified tandem and sequentially from the cervical vertebra toward the pelvis;
a correction step (3-Z) of conducting the correction by which the region A classified to the pelvis side is replaced by the region B when the region A, the region B and the region C are classified in tandem and sequentially from the cervical vertebra toward the pelvis;
a correction step (4-Z) of conducting the correction by specifying a y-coordinate from the region C to the region A or the region B as an upper side of the vertebral body when the region C, the region A or the region B are classified in tandem and sequentially from the cervical vertebra toward the pelvis, as a longitudinal direction extending between the cervical vertebra and the pelvis is a y-direction up-and-down, in the classification at a time after the correction (3); and
specifying the y-coordinate from the region A or the region B to the region C as a lower side of vertebral body when the region A, the region B and the region C are classified in tandem and sequentially from the cervical vertebra toward the pelvis;
specifying the y-coordinate from the region B to the region A as the upper side of a next vertebral body; and further specifying a (y-1)-coordinate of one previous pixel located in the cervical vertebral side from the upper side of the next vertebral body as a bottom side of vertebral body, when the region B and the region A are classified sequentially from the cervical vertebra toward the pelvis; and
conducting repeatedly the process to divide relative to other vertebrae as a temporal boundary and obtaining a total length in the y-direction relative to only the vertebral body from the y-coordinates of the upper side and the bottom side of vertebral bodies divided by conducting repeatedly;
specifying a value obtained by dividing said total length by a known number of vertebral bodies of vertebral images as an average length of vertebral body;
ranking each actual length of each said vertebral body based on an obtained average length of vertebral body; and
conducting a processing to coalesce the vertebral body having a shorter length in order with either an upper or a lower vertebral body repeatedly until no vertebral body less than a predetermined ratio of the average length of said vertebral body remains or until the number of the divided vertebral bodies becomes the same as said known number;
a correction step (5-Z) of conducting the correction of specifying the longitudinal direction extending between the cervical vertebra and the pelvis as the up-and-down y-direction; obtaining each distance between right and left of a sideline profiling the vertebral body per pixel line adjacent to definite number of pixels each other up-and-down from the boundary as the center at the y-coordinate from the region B to the region A and along the boundary, when a region B $R_B$ and a region A $R_A$ are classified sequentially from the cervical vertebra toward the pelvis;
obtaining the y-coordinate at the pixel line having the shortest distance; and
correcting newly such y-coordinate as the boundary from the region B $R_B$ to the region A $R_A$.

5. The image processing method according to claim 2, comprising the steps of:
correcting newly the boundary, wherein in a case of a failure to detect the intervertebral region, when the boundary contacting to the cervical vertebra side of the pedicle of vertebral arch is specified as the boundary between adjacent vertebral bodies and each other, setting each distance between right and left of a sideline adjacent to a definite number of pixels in each cervical vertebra side and the pelvis side of the boundary as a center thereof and also profiling the vertebral body per pixel line along the boundary is obtained, and
specifying the pixel line having the shortest distance as the boundary between each respective said adjacent vertebral body.

* * * * *